US012629258B2

(12) United States Patent
Mawatari et al.

(10) Patent No.: US 12,629,258 B2
(45) Date of Patent: May 19, 2026

(54) ARTIFICIAL JOINT STEM AND METHOD FOR MANUFACTURING ARTIFICIAL JOINT STEM

(71) Applicants: SAGA UNIVERSITY, Saga (JP); KYOCERA CORPORATION, Kyoto (JP)

(72) Inventors: Masaaki Mawatari, Saga (JP); Iwao Noda, Kyoto (JP)

(73) Assignees: SAGA University, Saga (JP); KYOCERA Corporation, Kyoto (JP)

( * ) Notice: Subject to any disclaimer, the term of this patent is extended or adjusted under 35 U.S.C. 154(b) by 866 days.

(21) Appl. No.: 17/915,432

(22) PCT Filed: Mar. 30, 2020

(86) PCT No.: PCT/JP2020/014541
§ 371 (c)(1),
(2) Date: Sep. 28, 2022

(87) PCT Pub. No.: WO2021/199153
PCT Pub. Date: Oct. 7, 2021

(65) Prior Publication Data
US 2023/0147429 A1     May 11, 2023

(51) Int. Cl.
*A61F 2/36* (2006.01)
*A61F 2/30* (2006.01)
(Continued)

(52) U.S. Cl.
CPC .......... *A61F 2/3662* (2013.01); *A61F 2/3094* (2013.01); *A61L 27/32* (2013.01); *B05D 3/12* (2013.01); *B05D 5/02* (2013.01); *A61F 2002/30321* (2013.01); *A61F 2002/30324* (2013.01); *A61F 2002/30326* (2013.01); *A61F 2002/30971* (2013.01); *A61F 2310/00796* (2013.01)

(58) Field of Classification Search
CPC .... A61F 2/3662; A61F 2/367; A61F 2/30767; A61F 2002/30321
See application file for complete search history.

(56) References Cited

U.S. PATENT DOCUMENTS 5,370,698 A     12/1994  Heimke et al.
9,358,115 B2 *   6/2016  Slater .................... A61F 2/3662
(Continued)

FOREIGN PATENT DOCUMENTS

EP          1709943 A2     10/2006
FR          2923375 A1      5/2009
(Continued)

*Primary Examiner* — Brian A Dukert
(74) *Attorney, Agent, or Firm* — Procopio, Cory, Hargreaves & Savitch LLP

(57) ABSTRACT

In the present disclosure, an artificial joint stem includes a base and a coating film located on the base. The base includes a first region, a second region, and a third region located in sequence. The coating film contains a calcium phosphate-based material and an antimicrobial material. The coating film is located across the first region and the second region, and the third region is exposed from the coating film. The surface of the coating film located in the first region has a larger surface roughness than the surface of the base in the third region.

17 Claims, 8 Drawing Sheets

(51) Int. Cl.

| | |
|---|---|
| A61L 27/32 | (2006.01) |
| B05D 3/12 | (2006.01) |
| B05D 5/02 | (2006.01) |

(56) References Cited

U.S. PATENT DOCUMENTS

| | | | | |
|---|---|---|---|---|
| 10,814,039 B2 * | 10/2020 | Mawatari | ................ | A61L 27/54 |
| 2005/0221259 A1 | 10/2005 | Anderson | | |
| 2008/0044449 A1 | 2/2008 | McKay | | |
| 2011/0008407 A1 | 1/2011 | Gan | | |
| 2013/0138223 A1 | 5/2013 | Mawatari | | |
| 2015/0056264 A1 | 2/2015 | Gan | | |

FOREIGN PATENT DOCUMENTS

| | | | |
|---|---|---|---|
| JP | H06304186 | A | 11/1994 |
| JP | H10-155822 | A | 6/1998 |
| JP | 2001037792 | A | 2/2001 |
| JP | 2011-512959 | A | 4/2011 |
| JP | 2012-040194 | A | 3/2012 |
| WO | 2020040051 | A1 | 2/2020 |

* cited by examiner

ARTIFICIAL JOINT STEM AND METHOD FOR MANUFACTURING ARTIFICIAL JOINT STEM

TECHNICAL FIELD

The present disclosure relates to an artificial joint stem and a method for manufacturing the artificial joint stem.

BACKGROUND OF INVENTION

The use of biological implants for the treatment of both bone injuries and diseases is constantly expanding with an increase in active population and aging population. In such a situation, a known biological implant is provided with a coating from the view point of antimicrobial properties, fixation properties to a bone, and the like.

For example, Patent Document 1 describes a coating for a medical implant, wherein a part of the coating contains a bone-binding agent and an antimicrobial metal agent containing silver.

CITATION LIST

Patent Literature

Patent Document 1: JP 2011-512959 T

SUMMARY

In the present disclosure, an artificial joint stem includes a base and a coating film located on the base. The base includes a first region, a second region, and a third region located in sequence. The coating film contains a calcium phosphate-based material and an antimicrobial material. The coating film is located across the first region and the second region. The third region is exposed from the coating film. The surface of the coating film located in the first region has a larger surface roughness than the surface of the base in the third region.

In the present disclosure, a method for manufacturing an artificial joint stem includes a first surface roughening step and a coating film forming step. The first surface roughening step includes forming a rough surface on a first region of a base, the base including the first region, a second region, and a third region located in sequence. The coating film forming step includes forming the coating film containing a calcium phosphate-based material and an antimicrobial material on the rough surface and the base such that the coating film extends across the first region and the second region and the third region is exposed.

Alternatively, in the present disclosure, a method for manufacturing an artificial joint stem includes a preparing step, a first protecting step, a surface roughening step, a protective material removing step, a second protecting step, and a coating film forming step. The preparing step includes preparing a base in which a first region, a second region, and a third region are located in sequence. The first protecting step includes disposing a first protective material at the base, the first protective material covering the second region and the third region while the first region is exposed. The surface roughening step includes forming a rough surface on the exposed first region. The protective material removing step includes removing the first protective material. The second protecting step includes disposing a second protective material, the second protective material covering the third region while the first region and at least part of the second region are exposed. The coating film forming step includes forming a coating film containing a calcium phosphate-based material and an antimicrobial material on the rough surface and the base exposed from the second protective material.

DESCRIPTION OF EMBODIMENTS

Figure 1:
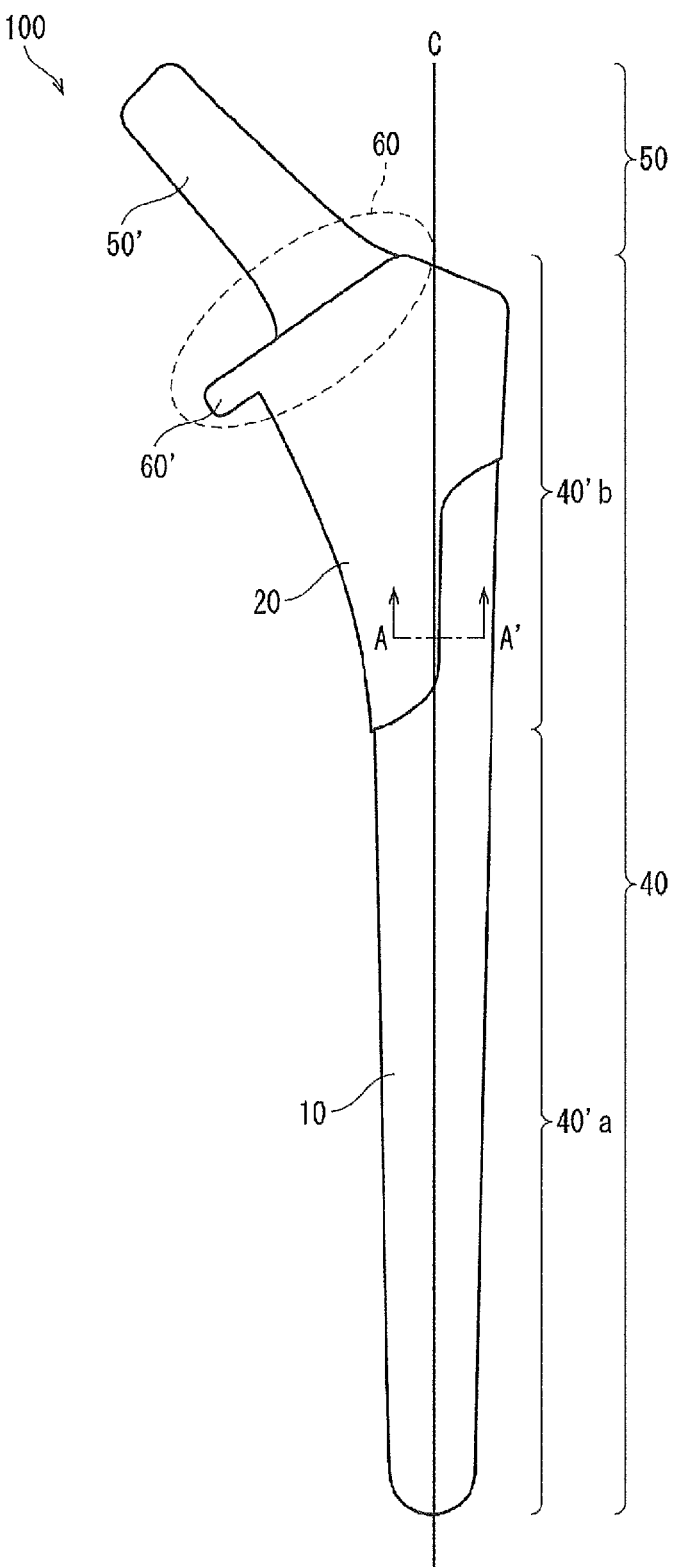
FIG. 1 is a schematic view illustrating an artificial joint stem according to an embodiment.

Hereinafter, one embodiment will be described in detail. Note that, unless otherwise specified in the present specification, "A to B", which represents a numerical range, means "A or more and B or less".

1. Artificial Joint Stem

First, a configuration of an artificial joint stem 100 according to an embodiment will be described with reference to FIGS. 1 and 2. The artificial joint stem 100 includes a base 10 and a coating film 20 located on the base 10. The coating film 20 contains a calcium phosphate-based material and an antimicrobial material. The artificial joint stem 100 further includes an embedded portion 40 to be embedded in a bone and an exposed portion 50 to be exposed from the bone.

Note that the calcium phosphate-based material has an effect of improving fixation properties to a bone. The antimicrobial material has an effect of reducing adhesion and growth of bacteria.

Figure 2:
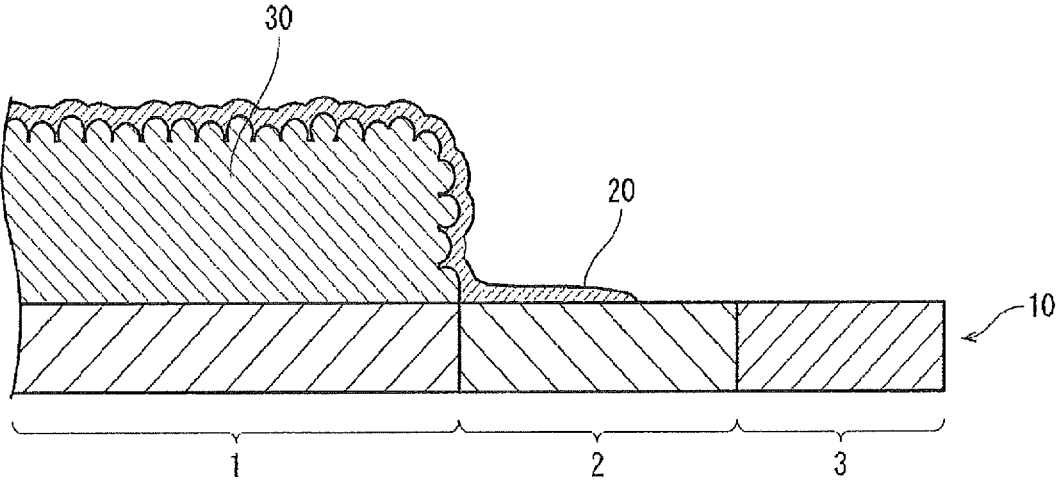
FIG. 2 is a schematic view illustrating a cross-section of an artificial joint stem according to an embodiment.

FIG. 2 is an enlarged view of a surface layer of a cross-section taken along A-A' in FIG. 1. The base 10 includes a first region 1, a second region 2 and a third region 3 located in sequence. The first region 1, the second region 2, and the third region 3 can be understood as being located in sequence in a direction parallel to the surface of the base 10. Note that, in FIGS. 2 to 5 and 7, the first region 1, the second region 2, and the third region 3 are hatched differently for descriptive purposes, but these regions need not be different components. The base 10 may be composed of one component. The first region 1, the second region 2, and the third region 3 can be distinguished in terms of design by, for example, the presence or absence of the coating film or the presence or absence of a rough surface to be described later. The coating film 20 is located across the first region 1 and the second region 2. The third region 3 is exposed from the coating film 20. The surface of the coating film 20 located in the first region 1 has a larger surface roughness than the surface of the base 10 in the third region 3.

Examples of surface roughness indices include arithmetic mean roughness Sa (ISO 25178). The surface roughness (Sa) of the coating film 20 located in the first region 1 may be set to, for example, 10 to 80 μm, or may be set to 20 to 80 μm, or may be set to 30 to 70 μm. The surface roughness (Sa) of the base 10 in the third region 3 is only required to be set to less than 1.0 μm, for example.

Note that the surface roughness Sa of the first region 1 can be determined based on the measurement result of the entire first region 1. The surface roughness Sa of the second region 2 can be determined based on the measurement result of the entire second region 2, and the surface roughness Sa of the third region 3 can be determined based on the measurement result of the entire third region 3. For example, the first region 1 may include a portion in which the surface roughness is locally smaller than the surface roughness of the base 10 in the third region 3, and the third region 3 may include a portion in which the surface roughness is locally larger than the surface roughness of the coating film 20 in the first region 1.

The surface roughness of the coating film 20 or the surface roughness of the base 10 is only required to be measured, for example, by a stylus method or an optical method. The surface roughness is only required to be measured in accordance with "ISO 25178", for example. Note that methods for measuring surface roughness are not limited to the above-described methods.

Here, there has been room for improvement in an artificial joint stem in terms of achieving the antimicrobial properties and the control of fixation properties to a bone in a compatible manner. That is, for example, in the case where the entire surface of an artificial joint stem is covered with a coating containing a bone-binding agent and an antimicrobial metal agent, the control of the fixation properties between the artificial joint stem and a bone is difficult. In this case, when the artificial joint stem has to be removed after surgery, there may be a difficulty in removing the artificial joint stem. For example, the embedded portion 40 may be excessively fixed to a bone via a coating.

In the present disclosure, the artificial joint stem 100 includes the coating film 20 located across the first region 1 and the second region 2, and the surface roughness of the coating film 20 in the first region 1 is larger than the surface roughness of the third region 3. Thus, the fixation properties to a bone and the antimicrobial properties can be sufficiently achieved. On the other hand, the third region 3 is exposed from the coating film 20, and the surface roughness of the third region 3 is smaller than the surface roughness of the first region 1. Thus, excessive fixation to a bone can be reduced. As described above, the artificial joint stem 100 can achieve the antimicrobial properties and the control of the fixation properties to a bone in a compatible manner.

The base 10 can be made of metal, ceramic, or plastic. Examples of the metal include stainless steel alloys, cobalt chromium alloys, titanium, and titanium alloys. As the titanium alloys, alloys added with at least one selected from the group consisting of aluminum, tin, zirconium, molybdenum, nickel, palladium, tantalum, niobium, vanadium, platinum, and the like can be used. Examples of the ceramic include alumina, zirconia, and alumina-zirconia composite ceramic. Examples of the plastic include polyethylene, fluorine-based resin, epoxy resin, polyetheretherketone (PEEK) resin, and Bakelite. Note that in the present embodiment, the base 10 is made of titanium alloy.

The base 10 may have, for example, a substantially rod shape, but the shape may be changed as appropriate depending on the shape of an artificial joint to be used.

At least part of the first region 1 is covered with the coating film 20. That is, the entire surface of the first region 1 may be covered with the coating film 20, or only part of the first region 1 may be covered with the coating film 20.

The surface of the coating film 20 located in the first region 1 has a larger surface roughness than the surface of the base 10 in the third region 3. Providing a region having a large surface roughness in this manner can improve the fixation properties to a bone. For example, the surface roughness of the coating film 20 located in the first region 1 can be increased by forming a rough surface in the first region 1 and covering the rough surface with the coating film 20.

Note that the surface roughness of the rough surface formed in the first region 1 is set to be larger than the surface roughness of the third region 3. Thus, the surface roughness of the coating film 20 located in the first region 1 can be made larger than the surface roughness of the third region 3. The surface roughness of the rough surface formed in the first region 1 may be set to 10 to 80 μm, or may be set to 20 to 80 μm, or may be set to 30 to 70 μm, for example. Note that the surface roughness of the rough surface can be measured, for example, by cutting the artificial joint stem 100 and observing the cut surface by an SEM or the like.

The artificial joint stem 100 may further include a layered member 30. The layered member 30 may be disposed on the first region 1. Accordingly, as illustrated in FIG. 2, the first region 1 is higher than a region where the layered member 30 is not provided (for example, the third region 3). Thus, when the artificial joint stem 100 is embedded in a bone, the first region 1 can primarily contact the bone. In the present specification, the "layered member" means a member that is stacked on the base 10 and is different from the coating film 20. For example, the surface of the layered member 30 may be rough. In this way, the region primarily in contact with a bone can have a rough surface. The layered member 30 may be formed by a thermal spraying method as described below. The layered member 30 may be formed to have a porous structure.

Note that the lower limit of the height of the layered member 30 is only required to be set to, for example, 100 μm or more, and may be set to 300 μm or more. The upper limit is only required to be set to, for example, 1000 μm or less, and may be set to 700 μm or less. The surface roughness of the layered member 30 may be set to, for example, 10 to 80 μm, or may be set to 20 to 80 μm, or may be set to 30 to 70 μm.

Note that the base 10 may be formed into a shape that enables the first region 1 to primarily contact a bone without the layered member 30. For example, the first region 1 may have a shape raised with respect to the second region 2 and the third region 3.

As a material of the layered member 30, the materials that have been exemplified as the material of the base 10 can be used. For example, the layered member 30 may be made of metal. The layered member 30 and the base member 10 may be made of the same material, or may be made of different materials. Accordingly, a sufficient strength can be achieved. Note that, in the present embodiment, the layered member 30 is formed of titanium alloy.

Figure 3:
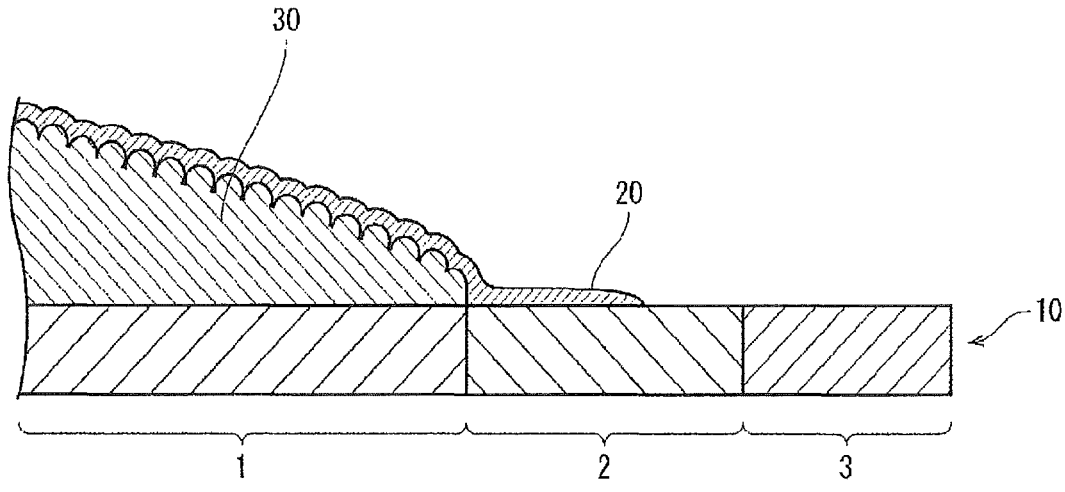
FIG. 3 is a schematic view illustrating a cross-section of an artificial joint stem according to an embodiment.

The layered member 30 may include an edge having a lower height than an inner portion of the layered member 30. In this specification, "an inner portion of the layered member" means an inner side of the layered member 30 in a surface direction. FIG. 3 illustrates the layered member 30 including an edge having a lower height than the inner portion. Accordingly, the concentration of stress at the edge of the layered member 30 can be reduced.

The coating film 20 contains a calcium phosphate-based material and an antimicrobial material. Examples of the calcium phosphate-based material include one type or two types or more of mixtures selected from the group consisting of hydroxyapatite, a-tertiary calcium phosphate, B-tertiary calcium phosphate, quaternary calcium phosphate, octacalcium phosphate, and calcium phosphate-based glass. As the antimicrobial material, a natural antimicrobial agent, an organic antimicrobial agent, or an inorganic antimicrobial agent can be used. For example, hinokitiol can be used as a natural antimicrobial agent, benzalkonium chloride can be used as an organic antimicrobial agent, and a metal can be used as an inorganic antimicrobial agent. Examples of the metal include silver, copper, and zinc. In addition to the calcium phosphate-based material and the antimicrobial material, the coating film 20 may contain a glass ceramic, and may further contain an antimicrobial agent such as penicillin and vancomycin.

The concentration of the antimicrobial material in the coating film 20 may be, for example, from 0.05 wt % to 3.00 wt %, from 0.05 wt % to 2.50 wt %, from 0.05 wt % to 1.00 wt %, or from 0.1 wt % to 1.00 wt %. When the concentration of the antimicrobial material is 0.05 wt % or more, sufficient antimicrobial properties can be achieved. When the concentration of the antimicrobial material is 3.00 wt % or less, the impact on living tissue can be reduced.

The coating film 20 may be disposed on the layered member 30. As described above, the layered member 30 can primarily come in contact with a bone. The coating film 20 is disposed on the layered member 30, which can further improve the fixation properties to a bone and the antimicrobial properties.

The height of the layered member 30 may be greater than the thickness of the coating film 20. Accordingly, the region in which the layered member 30 is formed becomes higher than the region in which only the coating film 20 is formed, and thus the region in which the layered member 30 is formed can primarily contact a bone. The thickness of the coating film 20 is only required to be set to, for example, less than 100 µm, and may be set to less than 50 µm. The thickness of the coating film 20 is only required to be set to, for example, 5 µm or more.

At least part of the second region 2 is covered with the coating film 20. That is, the entire surface of the second region 2 may be covered with the coating film 20, or only part thereof may be covered with the coating film 20. The second region 2 exists between the first region 1 and the third region 3. In the present specification, the coating film 20 is "located across the first region and the second region", which means that at least part of the boundary between the first region 1 and the second region 2 is covered with the coating film 20. That is, the entire boundary between the first region 1 and the second region 2 may be covered with the coating film 20, or only part thereof may be covered with the coating film 20. When the layered member 30 is disposed in the first region 1, the coating film 20 may extend from the first region 1 to the second region 2 so as to cover the edge of the layered member 30. That is, the edge of the layered member 30 can be covered so as not to be exposed from the coating film 20. Accordingly, bacterial growth can be further reduced.

Figure 4:
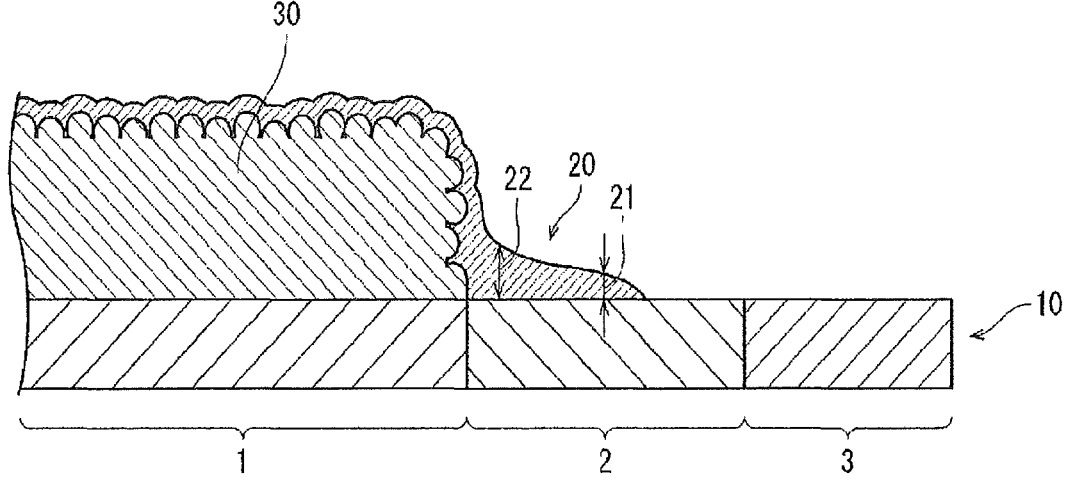
FIG. 4 is a schematic view illustrating a cross-section of an artificial joint stem according to an embodiment.

The coating film 20 located in the second region 2 may include an end portion 21 and a base portion 22 located closer to the first region 1 than the end portion 21 is to the first region 1. In the present specification, "the end portion of the coating film located in the second region" refers to a region of the coating film 20 located in the second region 2, the region being located closer to the boundary between the second region 2 and the third region 3. Also, "the base portion of the coating film located in the second region" refers to a region of the coating film 20 located in the second region 2, the region being located closer to the boundary between the first region 1 and the second region 2. Here, the thickness of the base portion 22 may be larger than the thickness of the end portion 21. FIG. 4 illustrates the coating film 20 in which the thickness of the base portion 22 is larger than the thickness of the end portion 21. Accordingly, the concentration of stress at and in the vicinity of the boundary between the first region 1 and the second region 2 can be reduced, and thus the peeling of the coating film 20 can be reduced. In the case where the layered member 30 is disposed in the first region 1, the concentration of stress at and in the vicinity of the edge of the layered member 30 can be reduced.

The third region 3 is exposed from the coating film 20. A region where the coating film 20 is disposed and a region exposed from the coating film 20 can be distinguished from each other by an elemental analysis of the surface of each region. A method for the elemental analysis can be performed, for example, by mapping surface elements using an energy dispersive X-ray (EDX) analyzer that is an auxiliary device of a typical scanning electron microscope (SEM). Surface analysis methods such as X-ray photoelectron spectroscopy, Auger electron spectroscopy, and secondary ion mass spectrometry may be used. A sample obtained by mechanically scraping off the surface of each region may be chemically analyzed for detection of elements. For example, phosphorus, calcium, antimicrobial components, and the like are detected from the surface of at least part of the first region 1 and the surface of at least part of the second region 2 where the coating film 20 is disposed. From the surface of the third region 3, elements constituting the base 10 are detected, and phosphorus, calcium, antimicrobial components, and the like are not detected, or are detected at a noise level or lower.

Figure 5:
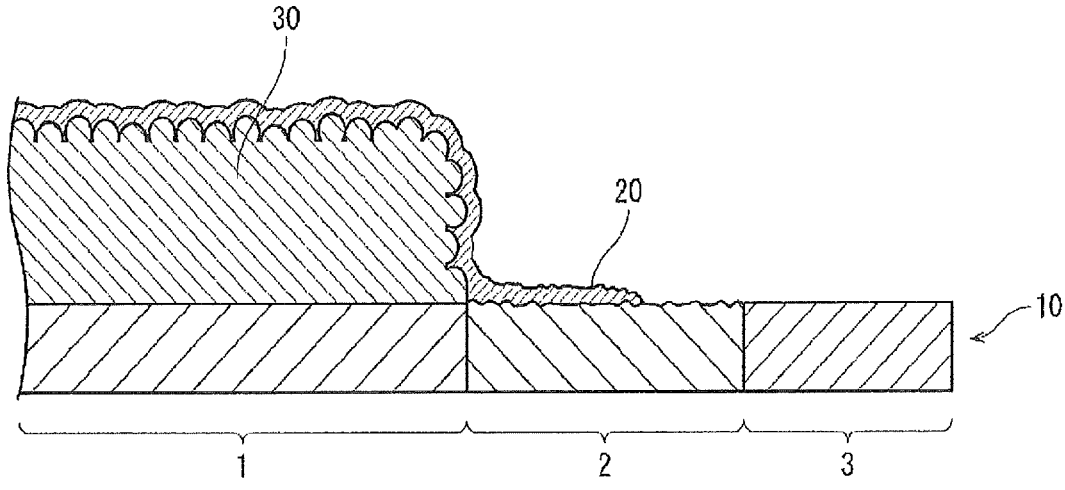
FIG. 5 is a schematic view illustrating a cross-section of an artificial joint stem according to an embodiment.

The surface of the coating film 20 located in the second region 2 may have a smaller surface roughness than the surface of the coating film 20 located in the first region 1. FIG. 5 illustrates an aspect in which the surface roughness of the coating film 20 located in the second region 2 is smaller than the surface roughness of the coating film 20 located in the first region 1. Accordingly, the fixation properties to a bone and the antimicrobial properties can be sufficiently achieved in the first region 1. Excessive fixation to a bone can be reduced in the second region 2.

Note that the surface roughness (Sa) of the coating film 20 located in the first region 1 may be set to, for example, 10 to 80 µm, or may be set to 20 to 80 µm, or may be set to 30 to 70 µm. The surface roughness (Sa) of the coating film 20 located in the second region 2 is only required to be set to, for example, 0.1 to 10 µm.

The surface of the coating film 20 located in the second region 2 may have a larger surface roughness than the surface of the base 10 in the third region 3. FIG. 5 illustrates an aspect in which the surface roughness of the coating film 20 located in the second region 2 is larger than the surface roughness of the base 10 in the third region 3. Accordingly, in the second region 2, the adhesion between the coating film 20 and the base 10 can be improved, and thus the fixation properties to a bone and the antimicrobial properties can be sufficiently achieved. Excessive fixation to a bone can be reduced in the third region 3. Note that the surface roughness (Sa) of the base 10 in the third region 3 is only required to be set to, for example, less than 1 µm.

As illustrated in FIG. 5, the surface roughness of the base 10 in the second region 2 may be larger than the surface roughness of the base 10 in the third region 3. Accordingly, in the second region 2, the adhesion between the coating film 20 and the base 10 can be improved, and thus the peeling of the coating film 20 can be reduced. Note that the surface roughness (Sa) of the base 10 in the second region 2 is only required to be set to 0.1 µm or more and less than 10 µm, and may be set to less than 2.0 µm.

In the present embodiment, the surface roughness of the rough surface of the base 10 in the first region 1 (including the rough surface of the layered member 30) is set to be larger than the surface roughness of the base 10 in the third region 3.

As described above, the base 10 may include the embedded portion 40 to be embedded in a bone and the exposed portion 50 to be exposed from the bone. Examples of the bone include a thighbone. The embedded portion 40 may include at least part of the first region 1. In other words, the coating film 20 may be formed at part of the peripheral wall of the embedded portion 40. Accordingly, desirable fixation properties and antimicrobial properties can be achieved in the embedded portion 40 that may actually contact a bone.

At least part of the coating film 20 may be disposed in a boundary region 60 including the boundary between the embedded portion 40 and the exposed portion 50. That is, the coating film 20 may be disposed in a region of the embedded portion 40 closer to the exposed portion 50. Accordingly, bacterial entry from the exposed portion 50 can be more efficiently reduced.

The coating film 20 disposed in the boundary region 60 may be disposed only at the embedded portion 40. That is, the coating film 20 need not be disposed on the exposed portion 50. Accordingly, irritation to soft tissue that may come in contact with the exposed portion 50 can be reduced.

The base 10 as described above may include a body portion 40' and a neck portion 50' connected to an upper end portion of the body portion 40. The body portion 40 includes a surface including the first region 1, the second region 2, and the third region 3. The body portion 40' may be embedded in a thighbone. The neck portion 50' is exposed from the thighbone, and may be provided with a bone head and installed in an acetabular cup that is paired with the artificial joint stem.

The body portion 40' includes a lower portion 40'a and an upper portion 40'b. The lower portion 40'a has a center axis C extending along a vertical direction. The upper portion 40'b extends in the vertical direction continuously from the lower portion 40'a and bends such that the center of the upper portion 40'b gradually departs further away from the center axis C as the upper portion 40'b extends more upward. Note that, for the vertical direction of the base 10, the upward direction corresponds to the proximal direction and the downward direction corresponds to the distal direction of a human body. The upper portion 40'b includes an upper end surface disposed offset from the center axis C, and the upper end surface is connected with the neck portion 50'. The neck portion 50' is smaller in width than the body portion 40' (the upper end surface). In other words, the neck portion 50' can be also referred to as a protruding portion 50' protruding from the body portion 40' in an oblique direction inclined from the center axis C.

The base 10 may further include a collar 60' provided at a connecting portion between the body portion 40' and the neck portion 50'. The collar 60' is a protruding portion protruding from the connecting portion in a surface direction of the upper end surface. The collar 60' can reduce excessive insertion of the body portion 40' into a thighbone during surgery using the artificial joint stem.

2. Method for Manufacturing Artificial Joint Stem

A method for manufacturing an artificial joint stem according to an embodiment includes a first surface roughening step and a coating film forming step. The first surface roughening step is a step of forming a rough surface on the first region 1 of the base 10, the base 10 including the first region 1, the second region 2, and the third region 3 located in sequence. The coating film forming step is a step of forming the coating film 20 containing a calcium phosphate-based material and an antimicrobial material on the rough surface and the base 10 such that the coating film 20 extends across the first region 1 and the second region 2 and the third region 3 is exposed. Accordingly, as described above, an artificial joint stem can be obtained in which the coating film 20 is located so as to extend across the first region 1 and the second region 2, the third region 3 is exposed from the coating film 20, and the surface of the coating film 20 located in the first region 1 has a larger surface roughness than the surface of the base 10 in the third region 3.

In the first surface roughening step, the rough surface can be formed by at least one selected from the group consisting of thermal spraying, additive manufacturing, chemical etching, and blasting. The thermal spraying, the additive manufacturing, or the chemical etching can produce larger surface roughness than the blasting. As materials for the thermal spraying and the additive manufacturing, the materials that have been exemplified as the materials of the base 10 can be used. The above-described layered structure may be formed by the thermal spraying or the additive manufacturing. Examples of the chemical etching include alkali treatment. Examples of the blasting include sandblasting. Note that the rough surface may be formed before the coating film 20 is formed.

The coating film 20 can be formed by thermal spraying such as flame spraying, high-speed flame spraying, and plasma spraying; physical vapor deposition or chemical vapor deposition such as sputtering, ion plating, ion beam deposition, and ion mixing; or wet coating such as sol-gel processing. The coating film 20 may be formed to cover at least part of the embedded portion 40.

A protective material may be used to form the rough surface or the coating film 20 only in a desired region. For example, a masking tape or a screen may be used as a protective material. Alternatively, a jig covering the base 10 may be used as a protective material. Examples of materials of these protective materials include a metal, a glass, a resin, and a composite thereof.

Note that the protective material may be or need not be in contact with the base 10. When the protective material is not in contact with the base 10, some quantity of a thermal spraying material, a coating film material, or the like may enter a region covered with the protective material from around an edge of the protective material and adheres to the region. Accordingly, the layered member 30 including the edge having a lower height than the inner portion thereof, the coating film 20 including the base portion 22 having a larger thickness than the end portion 21, and/or the like, may be formed as described above. As the protective material, for example, a masking tape having adhesiveness and capable of being attached to the base 10, or a jig covering the base 10 described below can be used.

In the case where a screen is disposed, the rough surface or the coating film 20 can be formed in a specific region by moving the position of the screen each time the rough surface or the coating film 20 is formed. In the case where a jig is used, the rough surface or the coating film 20 can be formed in a specific region by changing a region covered by the jig each time the rough surface or the coating film 20 is formed. In this case, the rough surface or the coating film 20 may also be selectively formed only in a desired region by, for example, adjusting the positional relationship between the screen and a discharge nozzle discharging a thermal spraying material or a coating material. In this case, a tip of the discharge nozzle is only required to be arranged, for example, in a straight line with the surface of the desired region without being separated by the screen. Note that the coating material means a material constituting the coating film. In the first surface roughening step, the surface of the first region 1 and the tip of the discharge nozzle is only required to be arranged in a straight line without being separated by the screen. In the coating film forming step, the surface of a region extending across the first region 1 and the second region 2 and the tip of the discharge nozzle is only required to be arranged in a straight line without being separated by the screen. In the case where the coating film 20 is formed simultaneously in the first region 1 and the second region 2, the tip of the discharge nozzle may be arranged, for example, in a straight line with the surface of the first region 1 without being separated by the screen in view of material diffusion. Without being limited to the above, the rough surface or the coating film 20 may be formed in a state where the base 10, the screen, and the discharge nozzle are fixed, or the rough surface or the coating film 20 may be formed while at least one selected from the group consisting of the base 10, the screen, and the discharge nozzle is moved. The rough surface or the coating film 20 may be formed with the angle of the discharge nozzle fixed or changed.

Note that the rough surface or the coating film 20 can be formed only in a desired region without using a protective material. For example, the rough surface or the coating film 20 can be selectively formed only in a desired region by adjusting the shape, the angle, the position or the like of the discharge nozzle discharging a thermal spraying material or coating material. For example, the thermal spraying material or the coating material may be discharged in a state where the discharge nozzle is located above the surface of the desired region. In the first surface roughening step, the thermal spraying material may be discharged in a state where the discharge nozzle is located above the surface of the first region 1. In the coating film forming step, the coating material may be discharged in a state where the discharge nozzle is located above the surface of the region extending across the first region 1 and the second region 2. In that case, the rough surface or the coating film 20 may be formed while the base 10 is fixed and the position and the angle of the discharge nozzle are changed, or the rough surface or the coating film 20 may be formed while the discharge nozzle is fixed and the position and the angle of the base 10 are changed. The discharge nozzle may be moved at a constant speed or at a variable speed. A discharge direction of the thermal spraying material or the coating material may form an angle of 90° or an angle of less than 90° with respect to a vector extending from the tip of the discharge nozzle toward the surface of the base 10 or the rough surface located at the shortest distance from the tip of the discharge nozzle.

For example, in the first surface roughening step, a first protective material may be disposed at the base 10 such that the second region 2 and the third region 3 are protected while the first region 1 is exposed, and the rough surface may be formed in the exposed first region 1. In the present disclosure, the manufacturing method may further include a step of removing the first protective material after the first surface roughening step and before the coating film forming step.

After the first protective material is removed, a step of cutting the edge of the rough surface, for example, the edge of the layered member 30 may be performed. Accordingly, the concentration of stress at the edge of the layered member 30 can be avoided, and irritation to living tissue can be reduced.

A first masking tape may be used as the first protective material. In that case, the manufacturing method according to the present disclosure may further include a step of attaching the first masking tape to the second region 2 and the third region 3 while exposing the first region 1 before the first surface roughening step.

In the coating film forming step, a second protective material may be disposed at the base 10 such that the first region 1 and a part of the second region 2 are exposed and the other part of the second region 2 and the third region 3 are protected, and the coating film 20 may be formed on the rough surface of the exposed first region 1 and the exposed second region 2. The second protective material can be removed after the coating film forming step. Here, a second masking tape may be used as the second protective material. In that case, the manufacturing method according to the present disclosure may further include a step of attaching, before the coating film forming step, the second masking tape to the other part of the second region 2 and the third region 3 while exposing the first region 1 and the part of the second region 2.

In the present disclosure, the manufacturing method may further include a second surface roughening step after the first surface roughening step and before the coating film forming step. In the second surface roughening step, a third protective material can be disposed at the base 10 such that the second region 2 is exposed and the third region 3 is protected, and a second rough surface may be formed in the exposed second region 2. In the second surface roughening step, the rough surface may be formed by at least one selected from the group consisting of chemical etching and blasting. The second surface roughening step may be performed such that the surface of the second rough surface formed in the second surface roughening step has a smaller surface roughness than a first rough surface in the first region 1. Note that in the case of forming the second rough surface, the rough surface in the first region 1 can also be referred to as the first rough surface. In the present disclosure, the manufacturing method may include a step of removing the third protective material after the second surface roughening step and before the coating film forming step.

A third masking tape may be used as the third protective material. In that case, the manufacturing method according to the present disclosure may further include a step of attaching the third masking tape to the third region 3 while exposing the first region 1 and the second region 2 before the second surface roughening step.

In the second surface roughening step, the first region 1 may be or need not be covered by a protective material. The first region 1 and the third region 3 may be protected and only the second region 2 may be processed by at least one selected from the group consisting of chemical etching and blasting. Alternatively, the third protective material may be disposed so as to expose the first region 1, and the rough surface of the exposed first region 1 and the second region 2 may be processed by at least one selected from the group consisting of chemical etching and blasting. Accordingly, an unnecessary thermal spraying material or the like remaining on the rough surface of the first region 1 can be removed and a rough surface can be formed in the second region 2.

Note that the second rough surface can be formed only in a desired region without using a protective material. For example, the second rough surface can be selectively formed only in a desired region by adjusting the shape, the angle, the position or the like of a discharge nozzle discharging a chemical etching material or blasting material. Note that the chemical etching material means a material that is discharged toward the base 10 in the case of performing processing by chemical etching. The blasting material means a material that is discharged toward the base 10 in the case of performing processing by blasting. For example, the chemical etching material or the blasting material may be discharged in a state where the discharge nozzle is located above the surface of the desired region. In the case where the second rough surface is formed only in the second region 2, the chemical etching material or the blasting material may be discharged in a state where the discharge nozzle is located above the surface of the second region 2. In the case where the second rough surface is formed in the first region 1 and the second region 2, the chemical etching material or the blasting material may be discharged in a state where the discharge nozzle is located above the surfaces of the first region 1 and the second region 2. In that case, the second rough surface may be formed while the base 10 is fixed and the position and the angle of the discharge nozzle are changed, or the second rough surface may be formed while the discharge nozzle is fixed and the position and the angle of the base 10 are changed. The discharge nozzle may be moved at a constant speed or at a variable speed. A discharge direction of the chemical etching material or the blasting material may form an angle of 90° or an angle of less than 90° with respect to a vector extending from the tip of the discharge nozzle toward the surface of the base 10 or the rough surface located at the shortest distance from the tip of the discharge nozzle.

For example, thermal spraying may be used in the first surface roughening step and the coating film forming step, and blasting may be used in the second surface roughening step. In that case, a material having a higher thermal resistance than the second protective material can be used as the first protective material. A material having a higher thermal resistance than the third protective material can be used as the first protective material. A material having a higher thermal resistance than the third protective material can be used as the second protective material. In order to satisfy the above-described relationship, for example, a material that is not dissolved or thermally decomposed for one minute at a thermal spraying condition of 8000° C. may be used as the first protective material, a material that is not dissolved or thermally decomposed for one minute at a thermal spraying condition of 3000° C. may be used as the second protective material, and a material that is not dissolved or thermally decomposed at a room temperature may be used as the third protective material. As specific examples of such materials, a composite material of a glass and a resin may be used as the first protective material, a composite material of a glass and a resin may be used as the second protective material, and a resin may be used as the third protective material.

In the case where a jig covering the base 10 is used as a protective material, the shape of the jig is not particularly limited, but may be, for example, tubular. The cross-section of a jig having a tubular shape may be polygonal, or may be circular.

Figure 7:
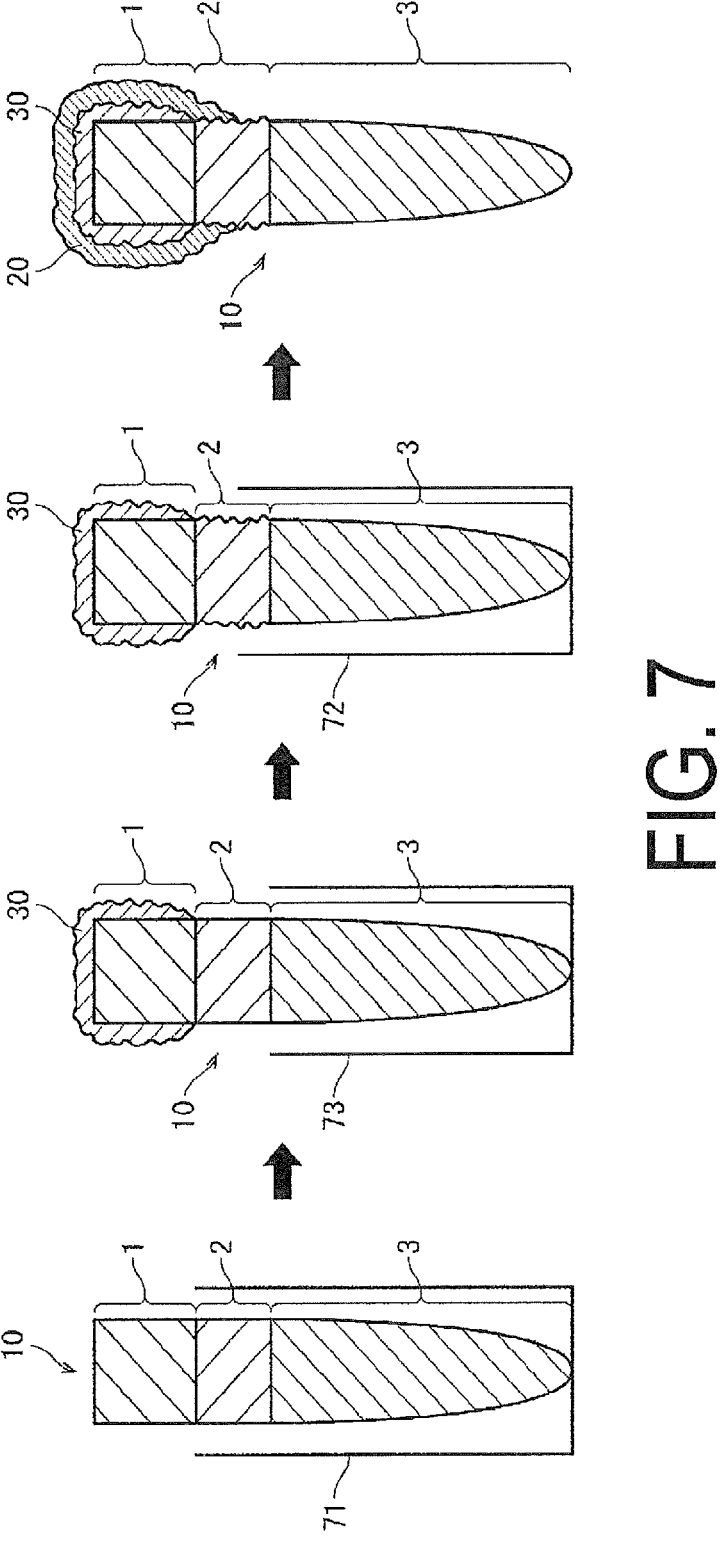
FIG. 7 is a schematic view illustrating a method for manufacturing an artificial joint stem according to an embodiment using a cylindrical jig.

An example in which a jig having a cylindrical shape is used will be described below. FIG. 7 is a schematic view illustrating a method for manufacturing an artificial joint stem according to an embodiment using a jig having a cylindrical shape. A jig 71 having a cylindrical shape and provided with an opening may be prepared as the first protective material. The base 10 can be secured to the jig 71 such that the second region 2 and the third region 3 of the base 10 are located inside the opening. Then, by performing the first surface roughening step, a rough surface can be formed in the first region 1 exposed from the jig 71. For example, the rough surface may be formed as the layered member 30. Next, a jig 73 having a cylindrical shape and provided with an opening may be prepared as the third protective material. The base 10 can be secured to the jig 73 such that the third region 3 of the base 10 is located inside the opening. Then, by performing the second surface roughening step, a rough surface can be formed in the second region 2 exposed from the jig 73. A jig 72 having a cylindrical shape and provided with an opening may be prepared as the second protective material. The base 10 can be secured to the jig 72 such that a part of the second region 2 and the third region 3 of the base 10 are located inside the opening. Then, by performing the coating film forming step, the coating film 20 can be formed on the layered member 30 of the first region 1 and on the other part of the second region 2 that are exposed from the jig 72.

In a step of forming the rough surface or the coating film 20 of the manufacturing method according to the present disclosure, a protective material may be disposed, in addition to the first protective material, the second protective material, and the third protective material described above. For example, in the step of forming the rough surface or the coating film 20, the protective material may be disposed on part or whole of the exposed portion 50. Accordingly, whether or not the rough surface or the coating film 20 is formed on the exposed portion 50 can be controlled as appropriate. For example, the coating film 20 can be formed on a region of the exposed portion 50 located closer to the embedded portion 40 by disposing the protective material in a region of the exposed portion 50 located further from the embedded portion 40 and forming the coating film 20 in an exposed region.

Figure 8:
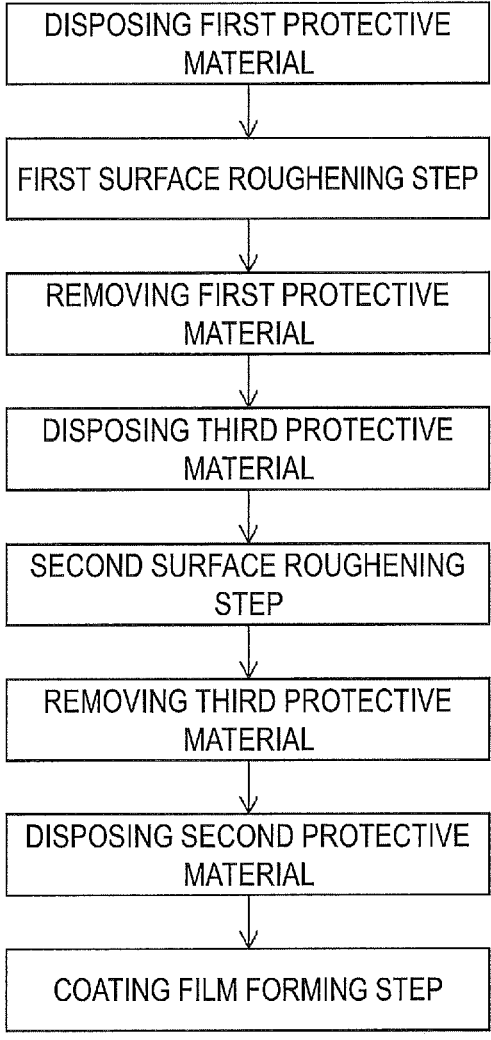
FIG. 8 is a flowchart illustrating a method for manufacturing an artificial joint stem according to an embodiment.

In summary, for example, the steps can be performed in the order illustrated in FIG. 8. FIG. 8 is a flowchart illustrating a method for manufacturing an artificial joint stem according to an embodiment. First, the first protective material is disposed, the first surface roughening step is performed, and then the first protective material is removed. Subsequently, the third protective material is disposed, the second surface roughening step is performed, and then the third protective material is removed. Then, the second protective material is disposed and then the coating film forming step is performed.

In the present disclosure, the manufacturing method may include or need not include a cleaning step between respective steps. For example, in the present disclosure, the manufacturing method may include a step of cleaning the base 10, or the base 10 and the layered member 30 disposed on the first region 1 after the first surface roughening step. The manufacturing method may further include a step of cleaning the base 10, or the base 10 and the layered member 30 disposed on the first region 1 after the second surface roughening step. A cleaning method is not particularly limited, and may be, for example, a method of immersing in a liquid such as water or an organic solvent such as alcohol, or may be a method of showering using the liquid. Alternatively, a method of blowing a gas such as air, nitrogen, or argon may be used. Accordingly, an unnecessary thermal spraying material and the like generated during the first surface roughening step and/or cutting chips and the like generated during the second surface roughening step can be removed.

In the present disclosure, the manufacturing method may be configured as follows. For example, in the present disclosure, the method for manufacturing the artificial joint stem may include a preparing step, a first protecting step, a surface roughening step, a protective material removing step, a second protecting step, and a coating film forming step. In the preparing step, the base 10 in which the first region 1, the second region 2, and the third region 3 are located in sequence can be prepared. In the first protecting step, the first protective material can be disposed at the base 10, the first protective material covering the second region 2 and the third region 3 while the first region 1 is exposed. In the surface roughening step, a rough surface can be formed on the exposed first region 1. In the protective material removing step, the first protective material can be removed. In the second protecting step, the second protective material can be disposed, the second protective material covering the third region 3 while the first region 1 and at least part of the second region 2 are exposed. In the coating film forming step, the coating film 20 containing a calcium phosphate-based material and an antimicrobial material can be formed on the rough surface and the base 10 exposed from the second protective material.

3. Use of Artificial Joint Stem

The artificial joint stem 100 illustrated in FIG. 1 has a shape mainly assumed to be the shape of an artificial hip joint stem, but an artificial joint to which the artificial joint stem according to the present disclosure is applied is not limited to an artificial hip joint. Examples of the artificial joint include an artificial hip joint, an artificial knee joint, an artificial ankle joint, an artificial shoulder joint, an artificial elbow joint, and an artificial finger joint.

Figure 6:
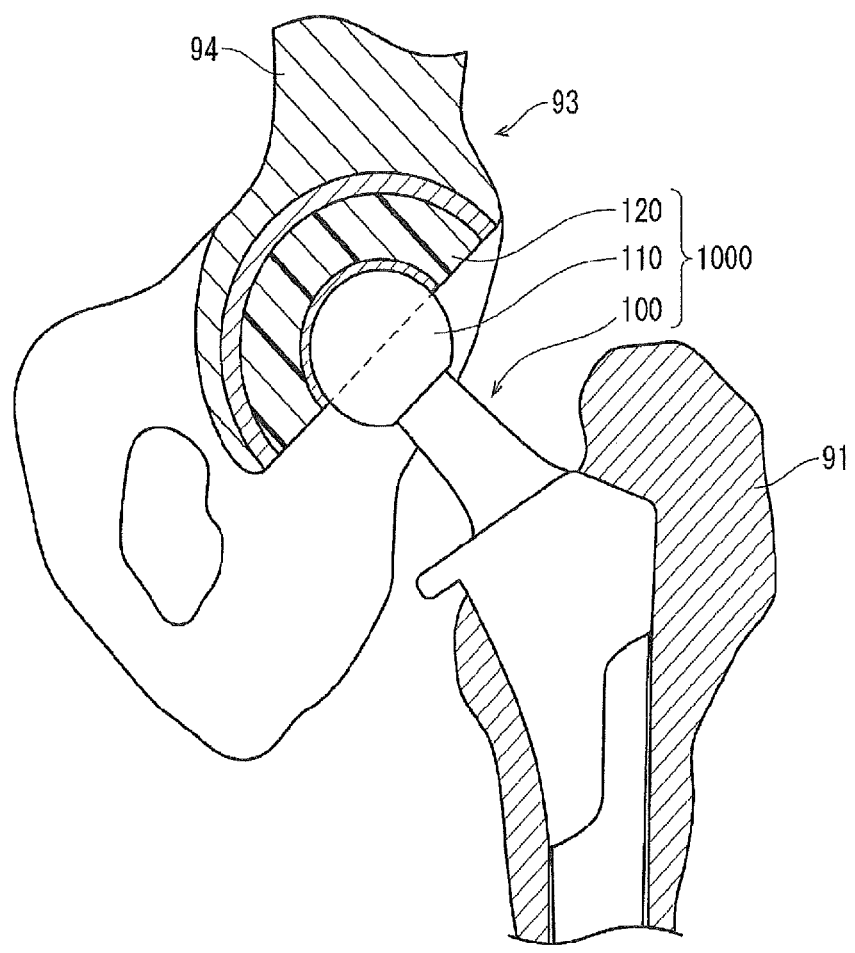
FIG. 6 is a schematic view illustrating an artificial hip joint according to an embodiment.

In the following, an example in which the artificial joint stem 100 is used as a part of an artificial hip joint 1000 will be described with reference to FIG. 6. The artificial hip joint 1000 may include a bone head 110 and an acetabular cup 120 in addition to the artificial joint stem 100. The bone head 110 and the acetabular cup 120 may be made of the same material as, or a different material from the material of the base 10 of the artificial joint stem 100. The artificial joint stem 100 is embedded in a thighbone 91. The bone head 110 is disposed at the exposed portion 50 of the artificial joint stem 100. The acetabular cup 120 is secured to an acetabulum 94 of a coxal bone 93. The bone head 110 fitted into a recess of the acetabular cup 120 is slid to function as a hip joint.

The invention according to the present disclosure has been described above based on the drawings and examples. However, the invention according to the present disclosure is not limited to each embodiment described above. That is, the invention according to the present disclosure can be variously modified within the scope indicated in the present disclosure, and an embodiment to be obtained by appropriately combining technical means disclosed in different embodiments is also included in the technical scope of the invention according to the present disclosure. In other words, note that a person skilled in the art can easily make various variations or modifications based on the present disclosure. Note that these variations or modifications are included within the scope of the present disclosure.

REFERENCE SIGNS

1 First region
2 Second region
3 Third region
10 Base
20 Coating film
21 End portion of coating film
22 Base portion of coating film
30 Layered member
40 Embedded portion
50 Exposed portion
60 Boundary region
100 Artificial joint stem
1000 Artificial hip joint

The invention claimed is:

1. An artificial joint stem comprising:
a base comprising a first region, a second region, and a third region located in sequence;
a layered member; and
a coating film located on the base, the coating film containing a calcium phosphate-based material and an antimicrobial material, wherein
the coating film is located across the first region and the second region,
the third region is exposed from the coating film,
a surface roughness of a surface of the coating film in the first region is larger than a surface roughness of a surface of the base in the third region,
the layered member is disposed on the first region and comprises an edge having a lower height than a height of an inner portion of the layered member.

2. The artificial joint stem according to claim 1, wherein the layered member is made of metal.

3. The artificial joint stem according to claim 1, wherein the coating film is disposed on the layered member.

4. An artificial joint stem comprising:
a base comprising a first region, a second region, and a third region located in sequence; and
a coating film located on the base, the coating film containing a calcium phosphate-based material and an antimicrobial material, wherein
the coating film is located across the first region and the second region,
the third region is exposed from the coating film,
a surface roughness of a surface of the coating film in the first region is larger than a surface roughness of a surface of the base in the third region,
the coating film located in the second region comprises an end portion and a base portion, the base portion being located closer to the first region than the end portion is to the first region, and
a thickness of the base portion is larger than a thickness of the end portion.

5. The artificial joint stem according to claim 1, wherein a surface roughness of a surface of the coating film located in the second region is smaller than a surface roughness of a surface of the coating film located in the first region.

6. The artificial joint stem according to claim 1, wherein a surface roughness of a surface of the coating film located in the second region is larger than a surface roughness of a surface of the base in the third region.

7. The artificial joint stem according to claim 1, wherein a surface roughness of the base in the second region is larger than a surface roughness of the base in the third region.

8. The artificial joint stem according to claim 1, wherein the base comprises an embedded portion to be embedded in a bone, and an exposed portion to be exposed from the bone, and the embedded portion comprises at least part of the first region.

9. The artificial joint stem according to claim 8, wherein at least part of the coating film is disposed in a boundary region comprising a boundary between the embedded portion and the exposed portion.

10. The artificial joint stem according to claim 9, wherein the coating film disposed in the boundary region is disposed only on the embedded portion.

11. An artificial hip joint comprising the artificial joint stem of claim 1.

12. A method for manufacturing an artificial joint stem, the method comprising:

a first surface roughening step of forming a rough surface on a first region of a base, the base comprising the first region, a second region, and a third region located in sequence; and a coating film forming step of forming a coating film on the rough surface and the base such that the coating film extends across the first region and the second region wherein the third region is exposed, and the coating film contains a calcium phosphate-based material and an antimicrobial material, wherein the coating film forming step comprises disposing a second protective material on the base such that a part of the second region and the third region are protected by the second protective material while the first region and an other part of the second region are exposed, and forming the coating film on the rough surface of the first region that is exposed and the other part of the second region that is exposed.

13. The method for manufacturing an artificial joint stem according to claim 12, wherein the first surface roughening step comprises disposing a first protective material on the base such that the second region and the third region are protected by the first protective material while the first region is exposed, and forming the rough surface in the first region that is exposed.

14. The method for manufacturing an artificial joint stem according to claim 12, wherein the first surface roughening step comprises forming the rough surface by at least one selected from the group consisting of thermal spraying and blasting.

15. The method for manufacturing an artificial joint stem according to claim 13, further comprising removing the first protective material after the first surface roughening step and before the coating film forming step.

16. The method for manufacturing an artificial joint stem according to claim 12, further comprising a second surface roughening step of disposing a third protective material on the base such that the third region is protected by the third protective material while the second region is exposed, and forming a second rough surface in the second region that is exposed, the second surface roughening step being performed after the first surface roughening step and before the coating film forming step.

17. The method for manufacturing an artificial joint stem according to claim 12, wherein the base comprises an embedded portion to be embedded in a bone, and an exposed portion to be exposed from the bone, and the coating film is formed to cover at least part of the embedded portion.

* * * * *